United States Patent
Bennet

(10) Patent No.: US 7,341,751 B2
(45) Date of Patent: Mar. 11, 2008

(54) EGGPLANT EXTRACT FOR MEDICAL TREATMENTS

(76) Inventor: Justin David Bennet, 3127 Valley La., Falls Church, VA (US) 22044

( * ) Notice: Subject to any disclaimer, the term of this patent is extended or adjusted under 35 U.S.C. 154(b) by 0 days.

(21) Appl. No.: 11/308,898

(22) Filed: May 23, 2006

(65) Prior Publication Data

US 2007/0275109 A1 Nov. 29, 2007

(51) Int. Cl.
*A61K 36/42* (2006.01)
*A61K 36/00* (2006.01)

(52) U.S. Cl. .................................................. 424/758
(58) Field of Classification Search ..................... None
See application file for complete search history.

(56) References Cited

U.S. PATENT DOCUMENTS

| 5,627,216 | A | 5/1997 | Papadopoulos | ............. | 514/783 |
| 6,638,540 | B2 | 10/2003 | Muhlbauer | ................. | 424/725 |

FOREIGN PATENT DOCUMENTS

| EP | 541796 | A1 | * | 5/1993 |
| JP | 57074059 | A | * | 5/1982 |
| JP | 2002226387 | A | * | 8/2002 |
| JP | 2003212785 | A | * | 7/2003 |
| KR | 2003088528 | A | * | 11/2003 |

* cited by examiner

*Primary Examiner*—Christopher Tate
*Assistant Examiner*—Deborah A. Davis
(74) *Attorney, Agent, or Firm*—Richard D. Fuerle

(57) ABSTRACT

An extract is made by cooking the fruit of an eggplant for about 15 to 30 minutes at about 120 to about 250° C., extracting the juice from the cooked fruit, and adding an oxidant to the juice that reacts with a component in it and changes its color from beige to black. Eggplants such as the Chinese eggplant and oxidants such as ferrous salts, such as ferrous sulfate, work particularly well. The extract can be formulated into various types of products, including pills, tablets, capsules, suppositories, foams, lotions, creams, and enema liquids. The products may be used for treating a variety of medical conditions, including gastrointestinal inflammation, hemorrhoids, skin inflammation, and other problems.

22 Claims, 1 Drawing Sheet

EGGPLANT EXTRACT FOR MEDICAL TREATMENTS

BACKGROUND OF THE INVENTION

This invention is related to the use of an eggplant extract to treat various medical conditions and diseases. In particular, it is related to an eggplant extract containing an iron oxidant and its use in medicine.

Eggplant is known to have medicinal properties and has been used in the treatment of skin diseases (Japanese Patent JP 2003-212785A), hemorrhoids (U.S. Pat. No. 5,627,216), and other medical conditions (U.S. Pat. No. 6,638,540). However, its use has not been extensive as its effectiveness has been limited.

SUMMARY OF THE INVENTION

I have found that the medical effectiveness of eggplant can be enhanced by mixing heated eggplant juice with an oxidant, such as an iron salt. The resulting extract can be formulated into various forms, such as pills, tablets, capsules, suppositories, foams, lotions, creams, and enema liquids for the treatment of a variety of medical conditions, including gastrointestinal inflammation, hemorrhoids, skin inflammation, and other problems.

DESCRIPTION OF THE PREFERRED EMBODIMENTS

Figure 1:
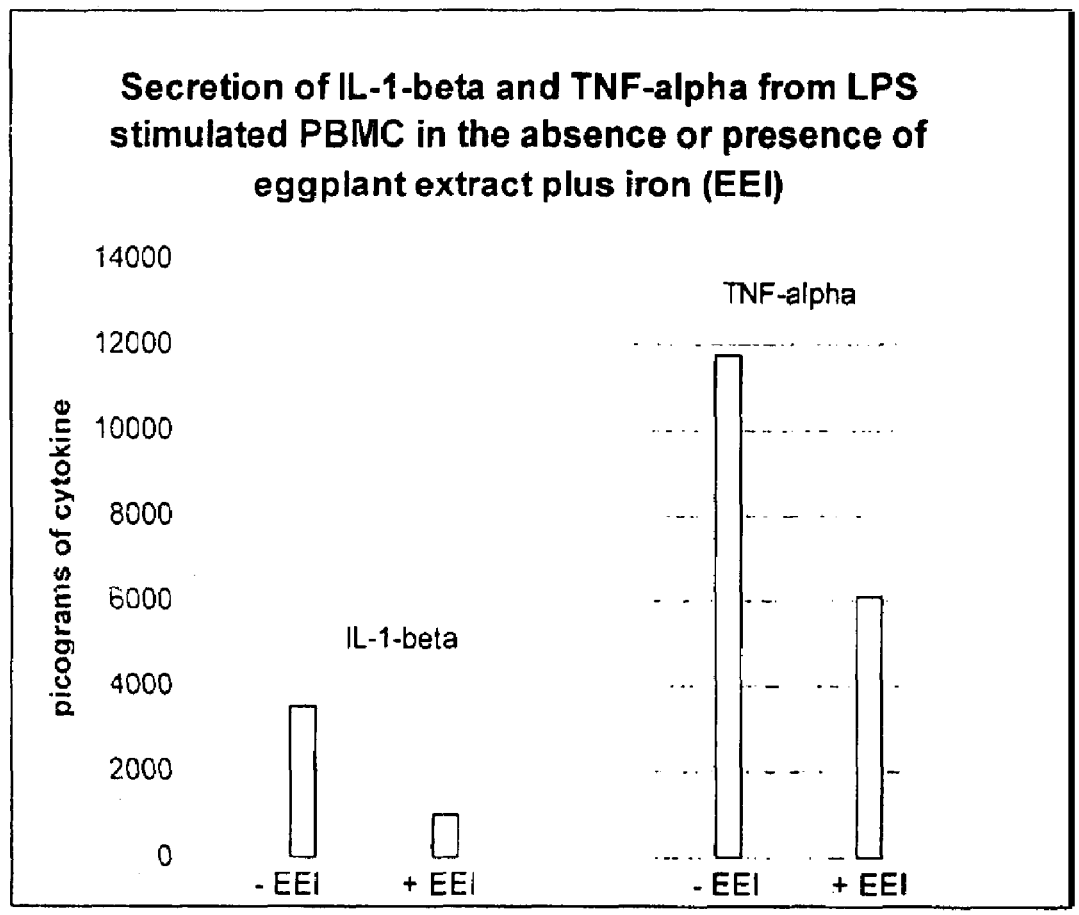
FIG. 1 is a graph that shows the results of adding eggplant extract plus iron to a donor's peripheral blood mononuclear cells.

The medicinal compositions of this invention are based on an extract prepared from eggplant, (*Solanum melongena* L. (Solanaceae)). Any variety of eggplant may be used, including the American eggplant (a purple, globular eggplant), the Chinese or Asian eggplant (an elongated, purple eggplant), the Japanese eggplant, the Italian eggplant, and the That eggplant (a small round green eggplant). and both the standard American eggplant and the Chinese or Asian eggplant are equally effective. However, the Asian varieties (e.g., Chinese, Japanese, and That) are preferred because some American eggplant extracts, when used as an enema, can produce cramping, but this was not observed when using extract from the Asian eggplants.

The fruit is the part of the eggplant that is used to prepare the extract of this invention. The fruit may be used with or without its skin. The fruit is preferably ripe so that the active components are fully developed.

The fruit is cooked until it softens, which typically requires about 15 to 30 minutes at about 120 to about 250° C. Cooking is necessary to make further processing easier (that is, it is much easier to obtain an aqueous juice from the cooked eggplant than from raw eggplant). Products made from cooked juice do not taste as bitter as those made from uncooked juice and, when used as an enema, the products do not cause cramping, as products made from uncooked juice can.

After the fruit has been cooked, it is pressed or centrifuged to obtain the juice. The juice may be strained to remove solids so that it is entirely a liquid or the pulp may be retained so that the juice is a mixture of solids and liquid. No pH adjustment is needed.

The medically active component of the juice is not known, but because eggplant has some medicinal effects when eaten, the active ingredient is likely to be a component of the juice that is present at a significant concentration. Since glycoproteins, proteins that are bonded to a sugar, are the only components of the juice of the eggplant fruit that are present at a significantly higher concentration than in other vegetables which do not have the same beneficial effect when eaten, it is believed that the active component is one or more glycoproteins. Other components of the eggplant juice, such as phenolic compounds, have been shown to have an anti-inflammatory activity, and that activity may be increased in the extract of this invention.

Once the cooked juice is obtained from the fruit, an extract is prepared from it by adding an oxidant to it. An oxidant is a compound that reacts with one or more of the active components in the eggplant juice, as indicated by a change in the color of the juice from beige (a pale to grayish yellow) to black. Compounds, such as oxygen gas or hydrogen peroxide, which do not produce that color change are not considered to be "oxidants" for the purposes of this invention. This change in color indicates both that the active component is present in the juice and that the oxidant has reacted with it to make it more effective. Fruit that does not change color, and compounds that do not change the color of the juice when added to it, should not be used to make the extract of this invention. While all the varieties of eggplant tested, including the That eggplant, a small round green eggplant, and the Italian eggplant, showed the reaction, other members of the same family (Solanaceae) as eggplants, including the potato (*Solanum tuberosum*), the tomato (*Lycopersicon esculentum* MILLER (Solanaceae), and red and green peppers (*Capsicum annuum* L. (Solanaceae), e.g., bell pepper, cherry pepper, cone pepper, green pepper, paprika, and sweet pepper, showed little or no reaction.

The preferred oxidant is a salt of iron. Ferrous salts are preferred because they are widely used in food additives and supplements and are generally believed to be safe, but ferric salts may also be used. Example of iron salts include ferric acetate, ferric albuminate, ferric and ammonium acetate solution, ferric citrate, ferric fructose, ferric glycerophosphate, ferric hypophosphate, ferric oxide saccharated, ferric phosphate, ferric sodium edetate, ferric sodium pyrophosphate, ferrocholinate, ferroglycine sulfate, ferronascin, ferrous bromide, ferrous carbonate mass, ferrous carbonate saccharated, ferrous chloride, ferrous citrate, ferrous fumarate, ferrous iodide, ferrous lactate, and ferrous succinate.

The anion of the salt should be medically acceptable so that it does not cause irritation, poisoning, or other medical problems. The preferred anion is sulfate because it has few adverse effects in animal testing. The amount of oxidant should be at least about 1 mg per liter (mg/l) of eggplant juice in order to oxidize at least a significant portion of the active component that is present in the juice, and more than about 50 mg/l is usually unnecessary; the preferred amount is about 10 to about 20 mg/l, as that amount is expected to oxidize most of the active component that is typically present in eggplant juice, thereby greatly increasing the activity of the extract; the color change usually goes to completion when at least 15 mg/l of the oxidant is used. At this stage the extract is a black liquid.

Once the extract is prepared, it is stabilized so that it does not degrade over time. This may be accomplished by, for example, freezing it, spray drying it, or freeze drying it, which keeps it stable for at least a year. If it is spray or freeze dried it should be sealed in a moisture-proof container to prevent the absorption of moisture, which may degrade it. The addition of a chemical stabilizer or pasteurization followed by sealing may also keep the extract active until it is used.

Optional components may also be added to the extract to enhance its effectiveness. About 0.1 to about 1000 mg/l (based on liters of extract) of an anti-inflammatory compound, such as a steroid (e.g., cortisol, cortisone, hydrocortisone, or prednisone), may be added to produce an additive or synergistic anti-inflammatory effect. About 0.1 to about 50 mg/l of an anti-oxidant, such as tocopherols, carotenoids, vitamin C, a synthetic anti-oxidant, e.g., butylated hydroxyl anisole (BHA), butylated hydroxyl toluene (BHT), may also be added. Pre- and pro-biotics, such as antibiotics, alpha-tocopherylquinone, lactobacilli, may also be added in an amount of about 1 to about 20 mg/l in order to provide additional anti-inflammatory and healing effects.

The extract may be administered orally, topically, as a suppository, as a rectal foam, or as an enema.

Oral

To use the extract orally, the liquid extract may be used full strength or diluted with water and mixed with flavoring, carbonation, sweeteners, etc. for drinking. The extract may also be freeze dried or spray dried and the dried extract added to water, tea, or other liquids.

The dried extract may be mixed with binders, excipients, colorants, etc. and formed into pills or tablets or placed inside capsules. An enteric coating, a pH dependent polymer, a polymer in a matrix, or a delayed release coating, such as "Eudrigit S," may be used to target the release of the extract at specific sites in the gastrointestinal tract. ("Eudrigit S" is a pH dependent copolymer of methacrylic acid and methyl methacrylate acrylic polymer made by Rohm Pharma GmbH, Weiterstadt, Germany, that is commonly used to make delayed release pills, either as a component of the matrix in which the active component is mixed or as a coating on the outside of the pill or capsule. The location in the gastrointestinal tract where the pill or capsule releases its active component can be approximately controlled because the permeability of the acrylic polymer is determined both by the pH of the fluid in which it is immersed and by the time of contact with the fluid.)

The dried extract may also be incorporated into a candy bar, food bar, or power bar along with substances typically used in those items, such as grains, fruits, flavorings, nuts, binders, etc. Orally, the extract reduces upper gastrointestinal inflammation such as gastritis, eosinophilic gastroenteritis, peptic ulcer disease, esophagitis and gastroenteritis.

The oral form is also effective in reducing gastrointestinal inflammation in the small intestine and colon, such as inflammation caused by Crohn's disease and ulcerative colitis Topical For topical use, the extract may be combined with fats, emulsifiers, oils, emollients, etc. to prepare a cream, lotion, lipophilic emulsion, or other topical formulation that is applied to the skin. The formulation may include lipophilic micellar compounds that increase the penetration of the components of the cream through the skin, such as "DifusiMax," a pluronic lecithin oranogel sold by Maxima Pharmaceuticals, Inc, Alberta, Canada. The amount of extract used in these formulations may be about 1 to about 1000 mg of extract per liter of formulation. Topical uses include the treatment of external hemorrhoids and inflammatory conditions of the skin, such as dermatitis, eczema, psoriasis, sunburn, and thermal burns.

Suppository

To use the extract as a suppository, it is compounded with fats, waxes, excipients, and binders, as is the usual practice in making suppositories. The suppository may contain about 1 to about 20 mg of extract per 50 mg of suppository. It is administered rectally and will dissolve at body temperature and deliver the active component to the colon. The suppository may be used to treat hemorrhoids, colitis, proctitis, and other conditions.

Rectal Foam

A rectal foam may be prepared by combining the extract with a foaming agent, such as cetyl alcohol, propylene glycol or lecithin. The amount of extract in the foam may be about 20 to about 500 mg per 10 mg of foaming agent. The foam may be administered into the rectum for the treatment of inflammation of the rectum and hemorrhoids.

Enema

The liquid extract may be diluted with water and used directly as an enema or it may be freeze dried or sprayed dried then reconstituted with water for use as an enema. An amount of extract of about 15 to about 150 mg per 200 ml may be used as an enema for treating colitis and proctitis of the large intestine, such as Crohn's disease and ulcerative colitis.

EXAMPLES

The following examples further illustrate this invention. In these examples, 2 to 4 kg standard American or Japanese eggplants were heated in a microwave oven at 1300 watts for 16 minutes. The resulting eggplant pulp (including the skin in the case of Japanese eggplant and without the skin in the case of American eggplant) was pressed in a hydraulic hand press. The juice collected was spun in a centrifuge at 1,000 times the force of gravity for 15 minutes and the supernatant juice was collected. For each 1 liter of supernatant juice, 15 mg of ferrous sulfate ("iron") was added.

A thin layer of this material, the eggplant extract plus iron, was frozen on the inside of a 1200 cc glass vacuum flask (i.e., shell frozen) overnight at $-20°$ C. The flask was attached to a Labconco 12 freeze dryer and a vacuum was applied. The ultimate vacuum was $10^{-4}$ mBar (meaning the vacuum attained by the vacuum pump and this system when no sample is attached to the machine). This is a manifold type freeze dryer, so the flask in which the sample is contained is exposed to room air. The room temperature was $75°$ F. The temperature of the sample and the vacuum present in the flask vary throughout the drying process depending on the rate of sublimation of water, thickness of the sample, time required for primary drying and secondary drying, etc. The eggplant extract plus iron was freeze dried for 24 to 48 hours. The resulting dried material was pulverized in a mortar and pestle and sealed in a moisture proof pouch.

At the time of use, the eggplant extract plus iron was reconstituted with 200 ml room temperature distilled water per 7 g eggplant extract plus iron. This was then either taken orally or used as an enema, depending on the study. In the Examples, 200 ml of the eggplant extract plus iron made as described above, or the direct extract plus iron without freeze drying and reconstitution, was used twice per day. In the hemorrhoid treatment study, the paste was made as described below.

The extract is fairly robust and a fairly wide variation around these parameters did not lessen the effectiveness of the eggplant extract plus iron. When the eggplant extract was spray dried in a Buchii 190 lab spray dryer using an inlet temperature of 130° C. and an outlet temperature of 65° C. the resulting powdered product had the same physical characteristics as the freeze dried material (its effectiveness in vivo was not tested).

Example 1

A patient having ulcerative colitis and hemorrhoids was treated as described in the following table. A patient in whom experimental skin inflammation was induced was also treated as described in the table below. For the oral treatment of ulcerative colitis and for use as an enema, 200 ml of water containing 7 g freeze dried eggplant extract with or without oxidant was used. The liquid extract was either fresh or was freeze dried then reconstituted with the same amount of water that is in the fresh extract (7 g extract per 200 ml water). The cream was made by mixing 5 g freeze dried extract plus oxidant with 5 ml water. No other additives were used in the hemorrhoid experiments. In one of the skin inflammation experiments, 100 ml of "DiffusiMax" was added to 5 g of extract in 5 ml of water.

TABLE 1

| Condition Treated | Ulcerative colitis | Ulcerative colitis | Ulcerative colitis | Hemorrhoids | Skin inflammation |
|---|---|---|---|---|---|
| Trial Substance | Extract (no iron) | Extract plus iron | Extract plus iron | Extract plus iron | Extract plus iron and "DiffusiMax" |
| Dosage | 200 ml liquid orally 3X/day | 200 ml liquid orally 2X/day | 200 ml liquid rectally 2X/day | 5 cc cream topically 2X/day | 3 cc cream topically 1X/day |
| Duration of Experiment | One year | One year | 3 months | One month | 2 days (repeated 3 times) |

| | | | Results | | |
|---|---|---|---|---|---|
| Outcome Measure | Simple Clinical Colitis Index (SCCI) | Simple Clinical Colitis Index (SCCI) | Simple Clinical Colitis Index (SCCI) | Hemorrhoid symptom index | Subjective assessment of inflammation |
| Score Before Treatment | 13 | 13 | 13 | 5 | Erythema, pain |
| Score After Treatment | 5 | 2 | 2 | 1 | No erythema No pain |

SCCI=Simple Clinical Colitis Index. The symptoms measured were stool frequency, stool frequency at night, urgency, blood in stool, general well being, and extraintestinal features. The score range was 0 to 18; a score of 2 or below indicates remission and a score of 5 or above indicates active disease.

HAI=Hemorrhoid Activity Index. The symptoms measured were pain, bleeding, and itching. The score range was 0 to 9. A score of 2 or below indicates remission and a score of 4 or above indicates active disease.

For eggplant extract and eggplant extract plus iron, benefit was achieved within one week of use. However, the anti-inflammatory activity of the extract was much greater for the extract plus iron than it was for the extract alone. In each experiment, after the benefit was achieved and the symptoms had stabilized, usage of the extract (or extract plus iron) was stopped. In each instance, all the symptoms returned. Symptoms were again reduced to the previous values within one week after restarting the same treatment. For the experiments involving treatment of ulcerative colitis, stopping and restarting was repeated at least five times with the same results.

Example 2

FIG. 1 and the following two tables show data from an in vitro experiment using PBMC from a healthy donor who provided peripheral blood mononuclear cells (PBMC) for this experiment. (PBMC are isolated from whole blood by gradient centrifugation. PBMC contain mostly lymphocytes and monocytes (neutrophils having been excluded by the separation procedure). They are commonly used to assess immune functions in vitro.)

The PBMC were stimulated with LPS. (LPS is lipopolysaccharide, a component of bacterial cell wall, which is commonly used as an antigen non-specific stimulator (also called a mitogen) of immune cell proliferation, synthesis and secretion. It is commonly used in vitro to simulate an immune response in vivo. Chemicals which block the LPS stimulated synthesis or secretion of pro-inflammatory mediators by immune cells (primarily lymphocytes and monocytes) may have similar activity in vivo and therefore may have anti-inflammatory activity in vivo.)

After 24 to 48 hours, the supernatant from each culture well was collected and assayed for the pro-inflammatory mediator noted (tumer necrosis factor (TNF)-alpha or IL-1-beta using a modified enzyme linked immunosorbent assay (ELISA). ("IL" is interleukin, a large series of chemical messengers used by the immune system to communicate between cells. They control immune cell migration, proliferation and secretion and various interleukins are involved in up regulating or down regulating the inflammatory response, depending on the particular interleukin.) These pro-inflammatory mediators are secreted by inflammatory cells upon stimulation and are involved in inflammatory reactions in vivo. The ability of eggplant extract with iron salt to suppress their secretion suggests that this is at least one mechanism through which the extract may exert its anti-inflammatory effect. Each assay was run in duplicate. Hydrocortisone is a positive control in that it is a known anti-inflammatory that suppresses the secretion of many inflammatory mediators.

The in vitro data on inhibition of cytokine secretion by PBMC's was done with PBMC's from a normal donor and with freeze dried eggplant extract plus iron made as described in Table 1 and used at the concentration shown in the cytokine inhibition table.

Table 2 provides additional information from the previous experiment. The table gives the actual raw data (picograms of substance being measured), the standard deviation between replicate experiments, and it shows the negative (no LPS) and positive (hydrocortisone) controls. This data demonstrates that the invention works as it should.

TABLE 2

Mean Cytokine Release and Standard Deviation Expressed in picograms of cytokine per $1 \times 10^6$ cells

| Drug | LPS | Mean IL-1 beta | Standard Deviation | Mean TNF-alpha | Standard Deviation |
|---|---|---|---|---|---|
| No Drug | −LPS | 0.0 | 0.0 | 24.8 | 2.2 |
| No Drug | +LPS | 3507.8 | 594.0 | 11753.0 | 446.1 |
| Hydro-cortisone | +LPS | 1757.8 | 370.4 | 298.8 | 106.4 |
| 0.25% eggplant extract + iron | +LPS | 1030.9 | 9.0 | 6088.0 | 670.2 |

The data in Table 3 is from the same experiment described in FIG. 1 and Table 2. The inflammatory mediator secretion is expressed as percent of maximal secretion (that is, in the presence of LPS and no eggplant extract or hydrocortisone). For example, in cell cultures in which LPS and eggplant extract plus iron was present, IL-1-beta secretion was only 29% of that in cultures where only LPS was present (and no eggplant extract plus iron was present). This is some of the same data as in the table above but presented in a way that clarifies how effective eggplant extract plus iron is in suppressing secretion of these inflammatory mediators.

TABLE 3

Mean and Standard Deviation of Released Cytokine Expressed in Percent of + LPS. (No Eggplant Plus Iron Sample)

| Drug | LPS | Mean IL-1-beta | Standard Deviation | Mean TNF-alpha | Standard Deviation |
|---|---|---|---|---|---|
| No Drug | −LPS | 0% | 0% | 0% | 0% |
| No Drug | +LPS | 100% | 17% | 100% | 4% |
| Hydro-cortisone | +LPS | 50% | 11% | 3% | 1% |
| 0.25% Eggplant Extract plus iron | +LPS | 29% | 0% | 52% | 6% |

Example 3

Skin inflammation was induced by treating the skin on the forearm of an individual with 0.1% capsaicin under an occlusive dressing for 4 hours, followed by treatment with a lotion made by mixing 5 g freeze dried eggplant extract plus powdered ferrous sulfate in 5 ml water to produce a paste. The paste was mixed with 25 ml of the hydrophilic phase of "DiffusiMAX" then 75 ml of the lipophilic phase of "DiffusiMax." An amount necessary to cover the inflamed area of skin was applied, approximately 2 cc on each arm. "DiffusiMax" alone was used as control.

Reduction in inflammation was measured after 4 hours, and was assessed by subjective assessment of pain, redness, and swelling. This experiment was repeated twice, and both times pain, redness, and swelling were significantly reduced in the arm treated with eggplant extract plus iron in "DiffusiMAX" as compared to the arm treated with "DiffusiMAX" alone.

What is claimed is:

1. A method of treating inflammation of the gastrointestinal track of a patient comprising
    (A) cooking the fruit of an eggplant until said fruit softens;
    (B) extracting juice from said fruit;
    (C) forming an extract by adding to said juice an oxidant that reacts with a component in said juice and changes the color of said juice from beige to black; and
    (D) orally or rectally placing said extract in the gastrointestinal track of said patient.

2. A method according to claim 1 wherein said oxidant is a salt of iron.

3. A method according to claim 1 wherein said salt of iron is selected from the group consisting of ferrous gluconate, ferrous sulfate, ferrous carbonate, ferrous bicarbonate, ferric chloride, and ferrous chloride.

4. A method according to claim 1 wherein said cooking is for about 15 to 30 minutes at about 120 to about 250° C.

5. A method according to claim 1 wherein said juice is extracted by pressing or centrifuging, followed by filtering.

6. A method according to claim 1 wherein said eggplant is an Asian eggplant.

7. A method according to claim 1 wherein said oxidant reacts with a glycoprotein in the juice of said eggplant, whereby said juice is made more effective in treating inflammation of the gastrointestinal track.

8. A method according to claim 1 wherein said extract is freeze or spray dried to form a solid powder.

9. A method according to claim 8 wherein said solid powder is made into a pill, tablet, or capsule.

10. A method according to claim 9 wherein said pill, tablet, or capsule is taken orally.

11. A method according to claim 8 wherein said powder is made into a suppository.

12. A method according to claim 11 wherein said suppository is administered rectally.

13. A method according to claim 8 where said powder is diluted in water and made into an solution to be taken orally.

14. A method according to claim 8 where said powder is diluted in water and made into a solution to be taken rectally as an enema.

15. A method of treating inflammation of the gastrointestinal track of a patient comprising
    (A) cooking the fruit of an eggplant for about 15 to 30 minutes at about 120 to about 250° C.;
    (B) pressing said cooked fruit to extract the juice therefrom;
    (C) straining the solids out of said juice;
    (D) forming an extract by adding to said juice about 5 to about 50 mg of a ferrous salt, whereby said ferrous salt reacts with a component in said juice and changes the color of said juice from beige to black; and
    (E) orally or rectally placing said extract in the gastrointestinal track of said patient.

16. A method according to claim 13 wherein said extract is dried and made into a pill, tablet, capsule, or powder.

17. A method according to claim 16 wherein said pill, tablet, capsule, or powder is taken orally.

18. A method according to claim 16 wherein said powder is made into a suppository or an enema.

19. A method according to claim 18 wherein said suppository or enema is administered rectally.

20. A method according to claim 16 wherein said extract is freeze or spray dried.

21. A method of treating inflammation of the gastrointestinal track of a patient comprising
- (A) cooking the ripe fruit of an eggplant for about 15 to 30 minutes at about 120 to about 250° C.;
- (B) pressing said cooked fruit to extract the juice therefrom;
- (C) straining the solids out, of said juice;
- (D) forming an extract by adding to said juice about 10 to about 20 mg ferrous sulfate per liter of said juice, whereby said ferrous sulfate reacts with a component in said juice and changes the color of said juice from beige to black;
- (E) stabilizing said extract by freezing, freeze drying or spray drying
- (F) forming said stabilized extract into a pill, tablet, capsule, or powder; and
- (G) orally or rectally inserting said pill, capsule, or powder into said patient.

22. A method according to claim 21 wherein said eggplant is an Asian eggplant.

\* \* \* \* \*